United States Patent
Uesaka et al.

(10) Patent No.: US 9,186,074 B2
(45) Date of Patent: Nov. 17, 2015

(54) SPHYGMOMANOMETER CUFF AND SPHYGMOMANOMETER

(75) Inventors: Chisato Uesaka, Kyoto (JP); Yoshihiko Sano, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 814 days.

(21) Appl. No.: 12/746,942

(22) PCT Filed: Dec. 8, 2008

(86) PCT No.: PCT/JP2008/072239
§ 371 (c)(1),
(2), (4) Date: Jun. 9, 2010

(87) PCT Pub. No.: WO2009/084375
PCT Pub. Date: Jul. 9, 2009

(65) Prior Publication Data
US 2010/0268099 A1    Oct. 21, 2010

(30) Foreign Application Priority Data
Dec. 28, 2007   (JP) .................................. 2007-339320

(51) Int. Cl.
A61B 5/02       (2006.01)
A61B 5/022      (2006.01)

(52) U.S. Cl.
CPC .................................. *A61B 5/02233* (2013.01)

(58) Field of Classification Search
USPC .................................................. 600/485–515
See application file for complete search history.

(56) References Cited

U.S. PATENT DOCUMENTS

| 5,997,540 A * | 12/1999 | Zheng et al. ..................... 606/64 |
| 6,645,157 B2 | 11/2003 | Inagaki |
| 6,997,878 B2 | 2/2006 | Inagaki et al. |
| 7,354,403 B2 * | 4/2008 | Mochizuki .................... 600/499 |

FOREIGN PATENT DOCUMENTS

| JP | 9-117419 A | 5/1997 |
| JP | 2002-209858 A | 7/2002 |
| JP | 2003-210423 A | 7/2003 |
| JP | 2004-195056 A | 7/2004 |

(Continued)

OTHER PUBLICATIONS

International Search Report w/translation from PCT/JP2008/072239 dated Jan. 6, 2009 (5 pages).

(Continued)

*Primary Examiner* — Michael Kahelin
*Assistant Examiner* — Mitchell E Alter
(74) *Attorney, Agent, or Firm* — Osha Liang LLP

(57) ABSTRACT

A sphygmomanometer cuff includes a fluid bag, a curved elastic member, a cushion material, and an outer package body. The fluid bag is arranged around an arm of a subject and compresses the arm. The curved elastic member is arranged to overlap an outer side of the fluid bag with respect to the arm, formed in a substantially tubular shape extending in a predetermined axial direction, and elastically deformable in a radial direction thereof. The cushion material is arranged at a position projecting from an end of the curved elastic member in the axial direction and more easily compression deformed than the curved elastic member. The outer package body accommodates the fluid bag, the curved elastic member, and the cushion material.

14 Claims, 15 Drawing Sheets

(56) References Cited

FOREIGN PATENT DOCUMENTS

| JP | 2004195056 | * | 7/2004 | |
| WO | WO2008044491 | * | 4/2008 | A61B 5/022 |

OTHER PUBLICATIONS

International Preliminary Report on Patentability from PCT/JP2008/072239 dated Sep. 28, 2009 (9 pages).

Patent Abstracts of Japan; Publication No. 2003-210423 dated Jul. 29, 2003 (1 page).

Patent Abstracts of Japan; Publication No. 09-117419 dated May 6, 1997 (1 page).

Patent Abstracts of Japan; Publication No. 2002-209858 dated Jul. 30, 2002 (1 page).

Patent Abstracts of Japan; Publication No. 2004-195056 dated Jul. 15, 2004 (1 page).

* cited by examiner

SPHYGMOMANOMETER CUFF AND SPHYGMOMANOMETER

TECHNICAL FIELD

The present invention generally relates to cuffs for sphygmomanometers and sphygmomanometers, and more specifically, to a sphygmomanometer cuff to be arranged around an upper arm of a subject when measuring a blood pressure, and a sphygmomanometer employing the sphygmomanometer cuff.

BACKGROUND ART

With regards to a conventional sphygmomanometer cuff, Japanese Unexamined Patent Publication No. 2002-209858 discloses an arm band of a sphygmomanometer aimed to include an elastic plate that is easily attached to an arm and exhibits excellent fitting property without giving pain after attachment (patent document 1). The arm band of the sphygmomanometer disclosed in patent document 1 includes the elastic plate that is arranged on the outer side of an air bladder and that has elasticity for holding an annular form of the arm band.

Japanese Unexamined Patent Publication No. 2004-195056 discloses a sphygmomanometer cuff aimed to be easily attached/detached to/from a measurement site such as an upper arm while being kept in a tubular form (patent document 2). In the sphygmomanometer cuff disclosed in patent document 2, a curved plate that is curved into a C-shape and can be elastically deformed in a radial direction, such as a synthetic resin plate, is arranged between an outer cloth and an ischemic air bladder. A sponge material is further arranged on the inner side of the curved plate.

Patent Document 1: Japanese Unexamined Patent Publication No. 2002-209858
Patent Document 1: Japanese Unexamined Patent Publication No. 2004-195056

DISCLOSURE OF THE INVENTION

Problem to be Solved by the Invention

As disclosed in patent documents 1 and 2, a curler (a elastic plate or a curved plate) for biasing an air bladder towards an arm is sometimes arranged in a sphygmomanometer cuff. The curler is an elastic body and has flexibility, but requires hardness of a certain extent to fit the sphygmomanometer cuff to the arm. In the sphygmomanometer cuff having such a configuration, an end of the curler in the axial direction of the arm touches the arm and the subject may feel pain if the subject adopts an attachment method of passing the tubular sphygmomanometer cuff from fingertips to the arm and sliding up to the measurement site.

In view of solving the above problem, it is an object of the present invention to provide a sphygmomanometer cuff and a sphygmomanometer in which satisfactory attachment feeling can be obtained when there is adopted the attachment method of passing the cuff from fingertips to an arm and sliding.

Means for Solving the Problem

A sphygmomanometer cuff according to one aspect of the present invention includes a fluid bag, a curved elastic member, a cushion material that more easily compression deforms than the curved elastic member, and an outer package body that accommodates the fluid bag, the curved elastic member, and the cushion material. The fluid bag is arranged around an arm of a subject and compresses the arm. The curved elastic member is arranged to overlap the outer side of the fluid bag with respect to the arm. The curved elastic member is formed in a substantially tubular shape extending in a predetermined axial direction, and is elastically deformable in a radial direction thereof. The cushion material is arranged at a position projecting from an end of the curved elastic member in the axial direction.

According to the sphygmomanometer cuff configured as described above, when the subject passes the sphygmomanometer cuff from the fingertips to the arm and slides to the measurement site (hereinafter simply referred to as in time of attaching the sphygmomanometer cuff), the cushion material touches the arm of the subject by way of the outer package body. The subject does not feel pain by the contact with the end of the curved elastic member, and a satisfactory attachment feeling can be obtained in time of attaching the sphygmomanometer cuff.

More preferably, the cushion material is fixed to the curved elastic member. According to the sphygmomanometer cuff configured as described above, positional shift of the cushion material with respect to the curved elastic member can be eliminated in time of attaching the sphygmomanometer cuff. Thus, the end of the curved elastic member is more reliably prevented from touching the arm of the subject.

More preferably, the cushion material is arranged so that the end of the cushion material and the end of the fluid bag are aligned with each other in the axial direction. According to the sphygmomanometer cuff configured as described above, the size of the outer package body can be avoided from becoming large due to the arrangement of the cushion material.

More preferably, the cushion material is made of a foamed sponge material or an elastomer. According to the sphygmomanometer cuff configured as described above, the cushion material having flexibility touches the arm of the subject in time of attaching the sphygmomanometer cuff, and thus a satisfactory attachment feeling can be obtained.

More preferably, the cushion material is arranged to cover the end of the curved elastic member. The cushion material is more preferably arranged between the curved elastic member and the fluid bag. According to the sphygmomanometer cuff configured as described above, the end of the curved elastic member is more reliably prevented from touching the arm of the subject in time of attaching the sphygmomanometer cuff.

More preferably, the cushion material is arranged integrally with the curved elastic member on an extension of the curved elastic member extending in the axial direction. According to the sphygmomanometer cuff configured as described above, the cushion material and the curved elastic member can be collectively handled in the assembly step of the sphygmomanometer cuff. Further, the task of inserting the cushion material into the outer package body can be smoothly carried out.

More preferably, the cushion material includes a first portion and a second portion arranged as members separate from each other. The end of the curved elastic member is sandwiched between the first portion and the second portion. According to the sphygmomanometer cuff configured as described above, the end of the curved elastic member can be reliably covered with the cushion material in a simple configuration.

More preferably, the cushion material extends from one end to the other end of the curved elastic member in the axial direction so as to shield the curved elastic member and the outer package body from each other. According to the sphygmomanometer cuff configured as described above, as the cushion material is interposed between the curved elastic member and the outer package body, a static friction resistance that occurs between the curved elastic member and the outer package body can be suppressed in a process of raising (pressurizing) or lowering (depressurizing) the pressure in the fluid bag. Sliding between the curved elastic member and the outer package body along with expansion and contraction of the fluid bag thus become smooth, and measurement accuracy of the blood pressure can be enhanced.

A sphygmomanometer cuff according to another aspect of the present invention includes a fluid bag, a curved elastic member, and an outer package body that accommodates the fluid bag and curved elastic member. The fluid bag is arranged around an arm of a subject and compresses the arm. The curved elastic member is arranged to overlap the outer side of the fluid bag with respect to the arm. The curved elastic member is formed into a substantially tubular shape extending in a predetermined axial direction, and is elastically deformable in a radial direction thereof. An end of the curved elastic member in the axial direction is provided with a curved surface that is curved at a position facing the arm.

According to the sphygmomanometer cuff configured as described above, when the subject passes the sphygmomanometer cuff from fingertips to the arm and slides to a measurement site, the curved surface touches the arm of the subject by way of the outer package body. Thus, the subject does not feel pain by the contact with the end of the curved elastic member, and a satisfactory attachment feeling can be obtained in time of attaching the sphygmomanometer cuff.

More specifically, the end of the curved elastic member has a circular cross-sectional shape. The end of the curved elastic member more preferably extends in the axial direction of the arm while warping in a direction of spaced apart from a surface in contact with the arm. According to the sphygmomanometer cuff configured as described above, a satisfactory attachment feeling can be obtained in time of attaching the sphygmomanometer cuff in a simple configuration of changing only the shape of the curved elastic member.

A sphygmomanometer according to the present invention employs one of the sphygmomanometer cuffs described above.

Effect of the Invention

As described above, the present invention provides a sphygmomanometer cuff and a sphygmomanometer capable of obtaining a satisfactory attachment feeling when attached in a method of passing the cuff from the fingertips to the arm and sliding to the measurement site.

DESCRIPTION OF SYMBOLS

Figure 1:
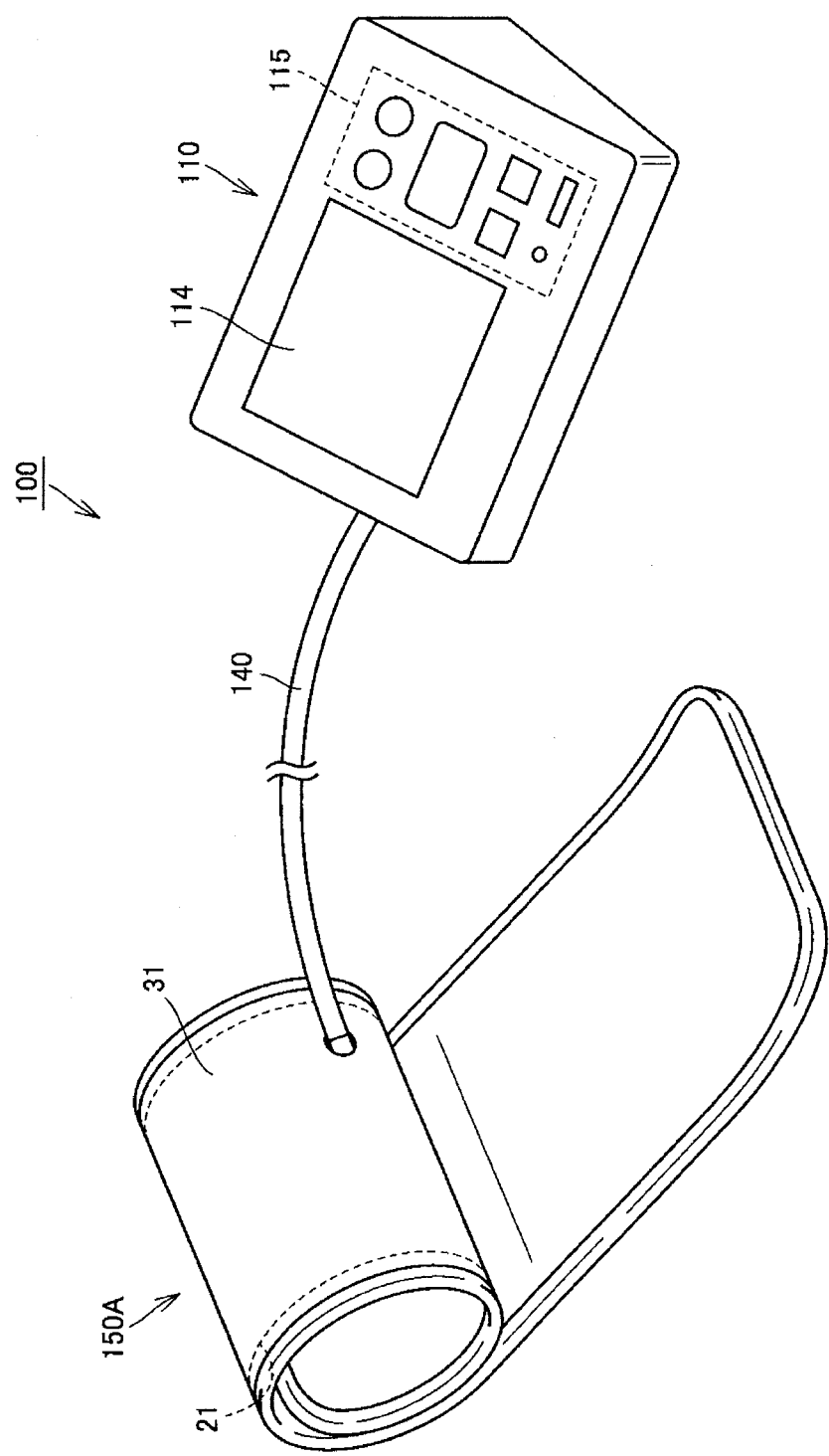
FIG. 1 is a perspective view showing an outer appearance of a sphygmomanometer.

11 curler
12, 13 end
12*a* curved surface
21 air bladder
31 bag-shaped cover body
51, 56, 61, 66, 71, 76, 81 cushion material
67 inner cushion material
68 outer cushion material
100 sphygmomanometer
150A, 150B sphygmomanometer cuff
200 arm

BEST MODE FOR CARRYING OUT THE INVENTION

Embodiments of the present invention will be described with reference to the drawings. In the drawings referenced below, the same symbols are denoted for the same or corresponding members. In the embodiments described below, description will be made exemplifying a sphygmomanometer cuff of an oscillometric upper arm type sphygmomanometer assuming an upper arm of a subject as a measurement site.

First Embodiment

FIG. 1 is a perspective view showing an outer appearance of a sphygmomanometer. The sphygmomanometer including a sphygmomanometer cuff according to a first embodiment of the present invention will be described first.

With reference to FIG. 1, a sphygmomanometer 100 includes a device main body 110 and a sphygmomanometer cuff 150A. The device main body 110 includes a display unit 114 and an operation unit 115. The display unit 114 visibly displays a measurement result of a blood pressure value, a measurement result of the number of pulses, and the like, in the form of numerical values, graphs, or the like. A liquid crystal panel or the like is used as the display unit 114. The operation unit 115 is arranged with a power button, a measurement start button, and the like.

The sphygmomanometer cuff 150A has an outer shape of a band, and is wrapped around an upper arm of a subject. The sphygmomanometer cuff 150A includes an air bladder 21 for compressing the upper arm, and a bag-shaped cover body 31 for wrapping and fixing the air bladder 21 around the upper arm. The air bladder 21 is accommodated in a space provided in the bag-shaped cover body 31. The structure of the sphygmomanometer cuff 150A will be described later in detail.

The air bladder 21 and the device main body 110 are connected with each other by an air tube 140 serving as a connection tube. The air tube 140 is made of a flexible tube, one end of which being connected to a blood pressure measurement air system component 131 (see FIG. 2, to be described later) arranged in the device main body 110, and another end of which being connected to the air bladder 21.

Figure 2:
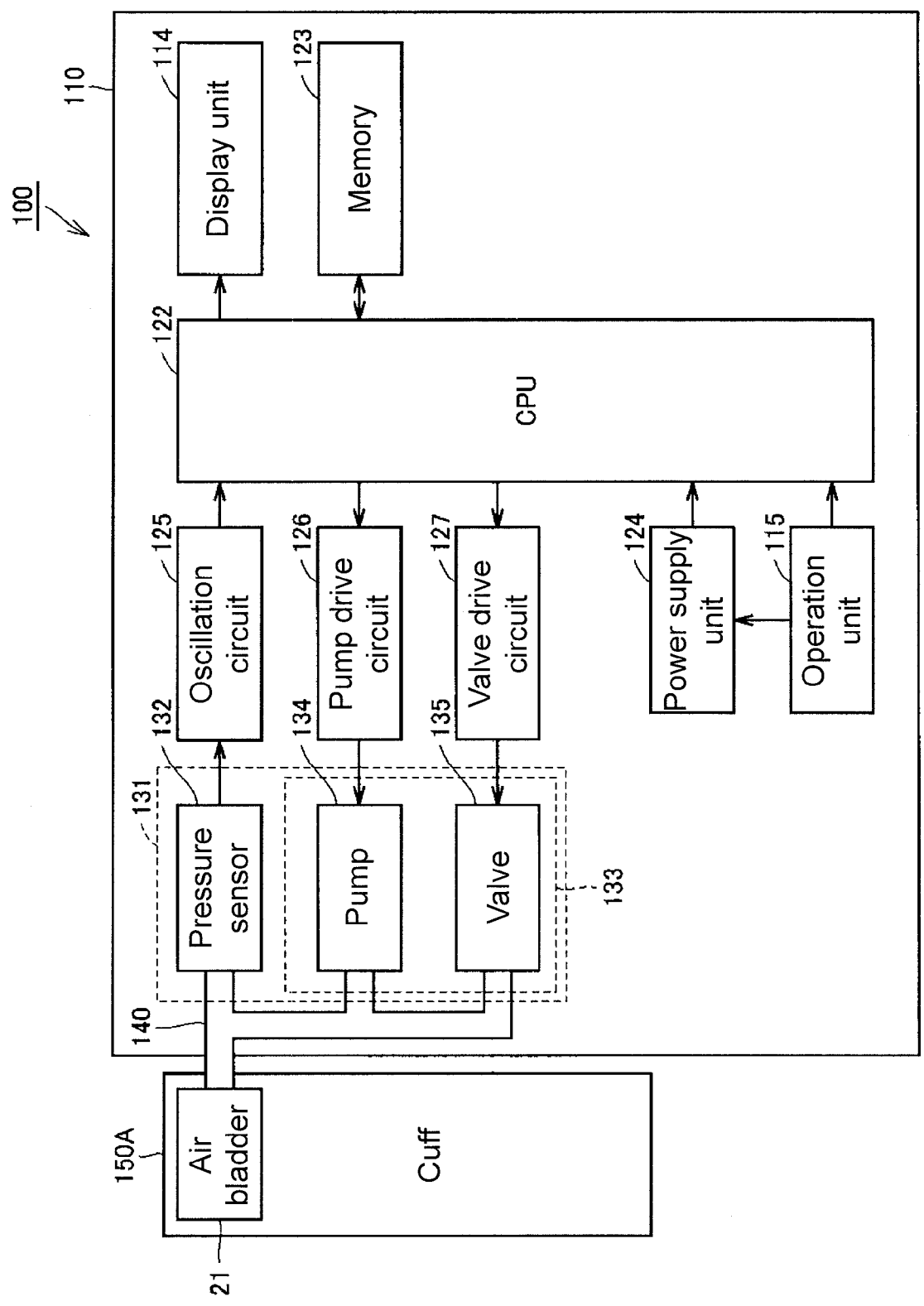
FIG. 2 is a functional block diagram showing a configuration of the sphygmomanometer in FIG. 1.

The configuration of main functional blocks of the sphygmomanometer 100 will be described next. FIG. 2 is a functional block diagram showing the configuration of the sphygmomanometer in FIG. 1.

With reference to FIG. 2, the blood pressure measurement air system component 131 for supplying/exhausting air through the air tube 140 to/from the air bladder 21 enclosed in the sphygmomanometer cuff 150A is arranged in the device main body 110 of the sphygmomanometer 100. The blood pressure measurement air system component 131 includes a pressure sensor 132 serving as pressure detection means for detecting a pressure in the air bladder 21, and a pump 134 and a valve 135 serving as expansion/contraction means 133 for expanding and contracting the air bladder 21. An oscillation circuit 125, a pump drive circuit 126, and a valve drive circuit 127 are arranged in the device main body 110 in relation to the blood pressure measurement air system component 131.

The device main body 110 includes a CPU (Central Processing Unit) 122 for controlling and monitoring each unit in a concentrated manner, a memory 123 for storing a program for causing the CPU 122 to perform a predetermined operation and various types of information such as a measured blood pressure value, a display unit 144 for displaying various types of information including a blood pressure measurement result, an operation unit 115 operated to input various types of instructions for measurement, and a power supply unit 124 for supplying power to the CPU 122 and the respective functional blocks. The CPU 122 functions as blood pressure value calculation means for calculating a blood pressure value.

The pressure sensor 132 detects a pressure in the air bladder 21 (hereinafter referred to as "cuff pressure"), and outputs a signal corresponding to the detected pressure to the oscillation circuit 125. The pump 134 supplies air to the air bladder 21. The valve 135 maintains the pressure in the air bladder 21, and also opens and closes when exhausting the air in the air bladder 21 and the like. The oscillation circuit 125 outputs to the CPU 122 a signal of an oscillation frequency corresponding to the output value of the pressure sensor 132. The pump drive circuit 126 controls to drive the pump 134 based on a control signal from the CPU 122. The valve drive circuit 127 controls to open/close the valve 135 based on a control signal from the CPU 122.

Figure 3:
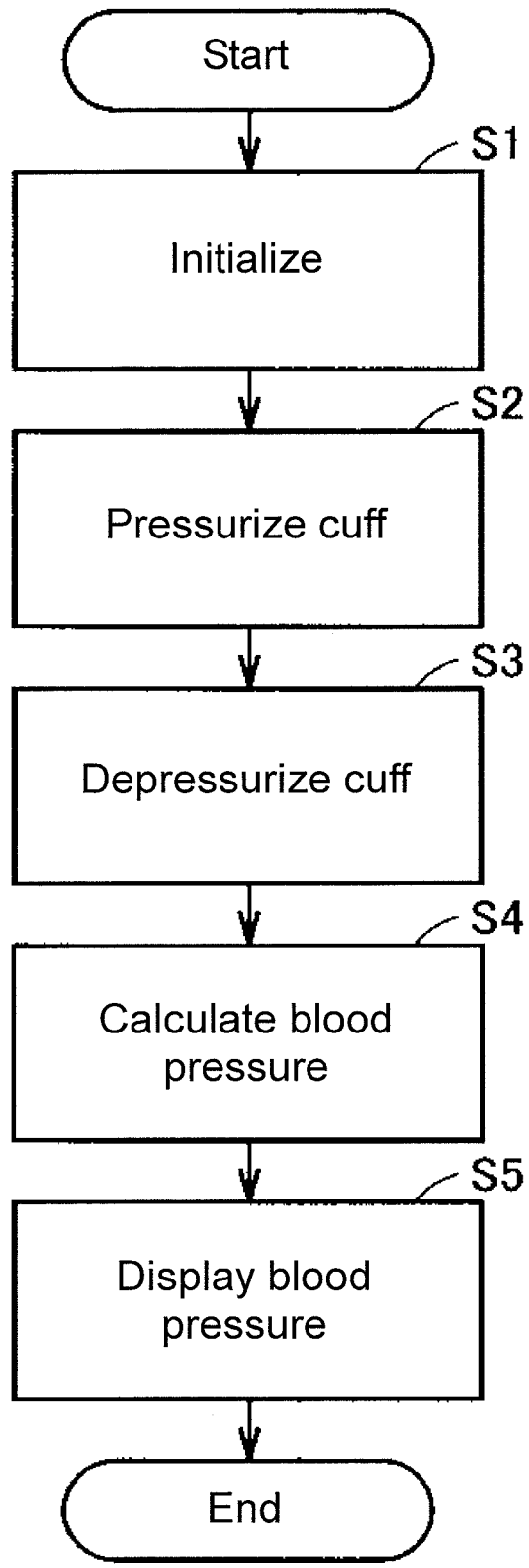
FIG. 3 is a flowchart showing a flow of a blood pressure measurement process of the sphygmomanometer in FIG. 1.

A flow of the blood pressure measurement process in the sphygmomanometer 100 will be described below. FIG. 3 is a flowchart showing the flow of the blood pressure measurement process of the sphygmomanometer in FIG. 1. The program according to the flowchart is stored in advance in the memory 123 shown in FIG. 2, and the blood pressure measurement process is performed when the CPU 122 reads out the program from the memory 123 and executes the same.

With reference to FIG. 2 and FIG. 3, when the subject operates an operation button of the operation unit 115 of the sphygmomanometer 100 to turn ON the power, the sphygmomanometer 100 is initialized (step S1). When being brought into the measurable state, the CPU 122 starts to drive the pump 134, and gradually raises the cuff pressure of the air bladder 21 (step S2). In the process of gradually pressurizing the cuff pressure, the CPU 122 stops the pump 134 when the cuff pressure reaches a predetermined level necessary for blood pressure measurement, gradually opens the closed valve 135 to gradually exhaust air in the air bladder 21 to gradually decrease the cuff pressure (step S3), where the cuff pressure is detected in the slow depressurization process of the cuff pressure.

The CPU 122 then calculates blood pressure values (systolic blood pressure value and diastolic blood pressure value) in a known procedure (step S4). Specifically, in the process of gradual decrease of the cuff pressure, the CPU 122 extracts pulse wave information based on the oscillation frequency obtained from the oscillation circuit 125. The blood pressure value is calculated from the extracted pulse wave information. After the blood pressure value is calculated in step S4, the calculated blood pressure value is displayed on the display unit 114 (step S5). The measurement method described above is based on the so-called depressurization measurement method of detecting a pulse wave in time of depressurization of the air bladder and calculating a blood pressure value, but there may obviously be adopted the so-called pressurization measurement method of detecting a pulse wave in time of pressurization of the air bladder and calculating a blood pressure value.

Figure 4:
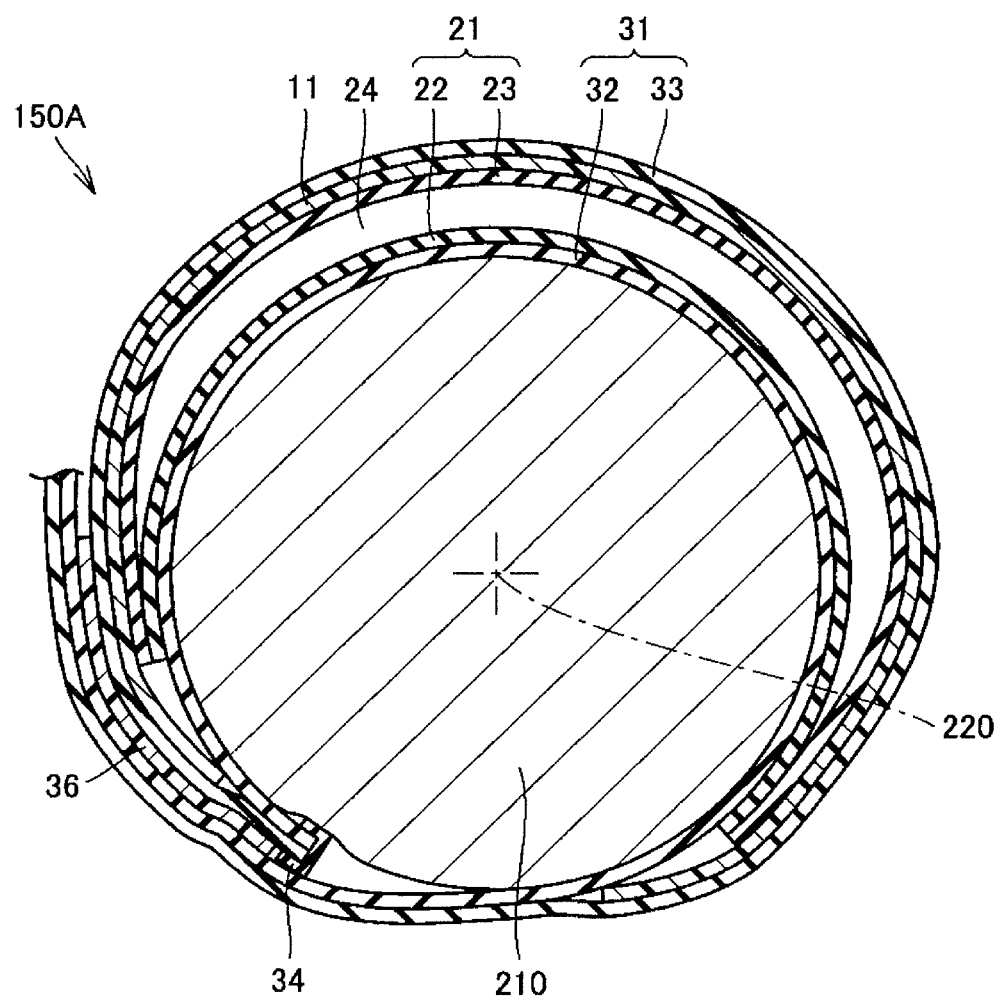
FIG. 4 is a cross-sectional view showing the sphygmomanometer cuff wrapped around an upper arm.

The structure of the sphygmomanometer cuff 150A will be described next in detail. FIG. 4 is a cross-sectional view showing the sphygmomanometer cuff wrapped around the upper arm.

With reference to FIG. 1 and FIG. 4, the air bladder 21 has an outer shape of a substantially rectangle in a developed state, and is preferably a bag-shaped member made of a resin sheet. The air bladder 21 includes a sheet member 22 that forms an inner wall portion positioned on a living body side, namely, an upper arm 210 in a state attached to the upper arm 210, and a sheet member 23 that forms an outer wall portion positioned on the outer side of the inner wall portion. An expansion/contraction space 24 is formed in the air bladder 21 by overlapping the sheet member 22 and the sheet member 23 and thermally welding the peripheral edges thereof. The previously described air tube 140 is connected to the expansion/contraction space 24.

The material for the resin sheet that forms the air bladder 21 may be of any kind as long as it excels in stretchability and air does not leak out from the expansion/contraction space 24 after welding. In view of this, the suitable materials for the resin sheet include ethylene-polyvinyl acetate copolymer (EVA), flexible polyvinyl chloride (PVC), polyurethane (PU), polyamide (PA), and raw gum.

The bag-shaped cover body 31 includes an inner cover member 32 configuring an inner exterior packaging positioned on the side of the upper arm 210 in the attached state to the upper arm 210, and an outer cover member 33 configuring an outer exterior packaging positioned on the side opposite to the upper arm 210 with the air bladder 21 interposed therebetween. The inner cover member 32 and the outer cover member 33 are overlapped with each other, and the peripheral edges thereof are joined together using a bias tape 34.

The bag-shaped cover body 31 is formed by a fabric preferably made of synthetic fibers such as polyamide (PA) or polyester. The inner cover member 32 of the bag-shaped cover body 31 is preferably configured by a member excelling in stretchability, and the outer cover member 33 of the bag-shaped cover body 31 is preferably configured by a member having poorer stretchability than the inner cover member 32.

A surface fastener 36 is arranged on an outer peripheral surface on one end in the longitudinal direction of the bag-shaped cover body 31, and the surface fastener 36 is engaged with an inner peripheral surface on another end in the longitudinal direction of the bag-shaped cover body 31. The surface fastener 36 serves as locking means for wrapping and fixing the sphygmomanometer cuff 150A around the upper arm 210 when the sphygmomanometer cuff 150A is attached to the upper arm 210, that is, the measurement site.

The sphygmomanometer cuff 150A includes a curler 11 for biasing the air bladder 21 inward. The curler 11 has a substantially rectangular outer shape in the developed state. The curler 11 is formed in a cylindrical shape extending in the axis direction of a center axis 220 serving as a virtual axis so as to fit to the upper arm 210, and is made of a flexible member configured to be elastically deformable in the radial direction by being annularly wrapped around. The curler 11 is arranged in the bag-shaped cover body 31 to overlap the outer side of the air bladder 21 with respect to the upper arm 210. The curler 11 is made of a resin material such as polypropylene (PP) so as to exhibit sufficient elastic force.

Figure 5:
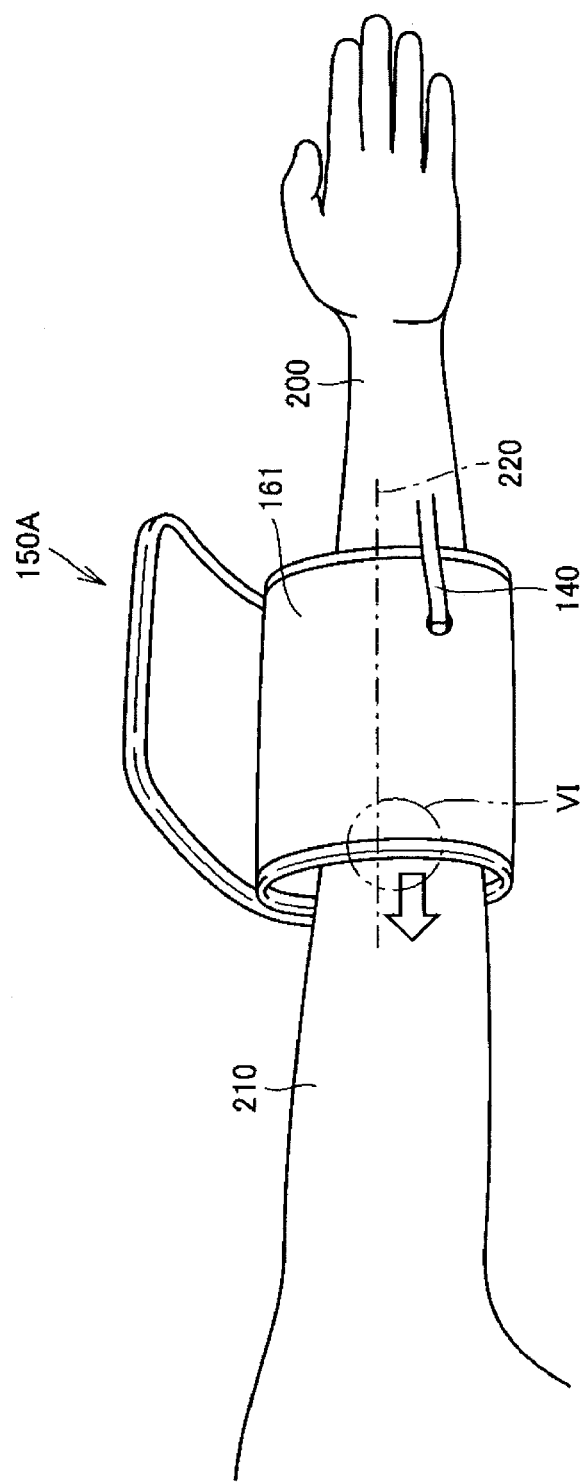
FIG. 5 is a view showing a state where a subject attaches the sphygmomanometer cuff in FIG. 4 to an upper arm.

FIG. 5 is a view showing a state where the subject attaches to the upper arm the sphygmomanometer cuff in FIG. 4. With reference to FIG. 5, a general attachment method of the sphygmomanometer cuff 150A includes placing the sphygmomanometer cuff 150A in the developed state to the upper arm 210, and engaging the surface fastener 36 to the inner peripheral surface of the bag-shaped cover body 31 while tightening the bag-shaped cover body 31 with respect to the upper arm 210. However, some subjects adopt a method of passing the sphygmomanometer cuff 150A in the tubular state from the fingertips through an arm 200 and sliding up to the upper arm 210 along the axis direction of the arm 200.

Figure 6:
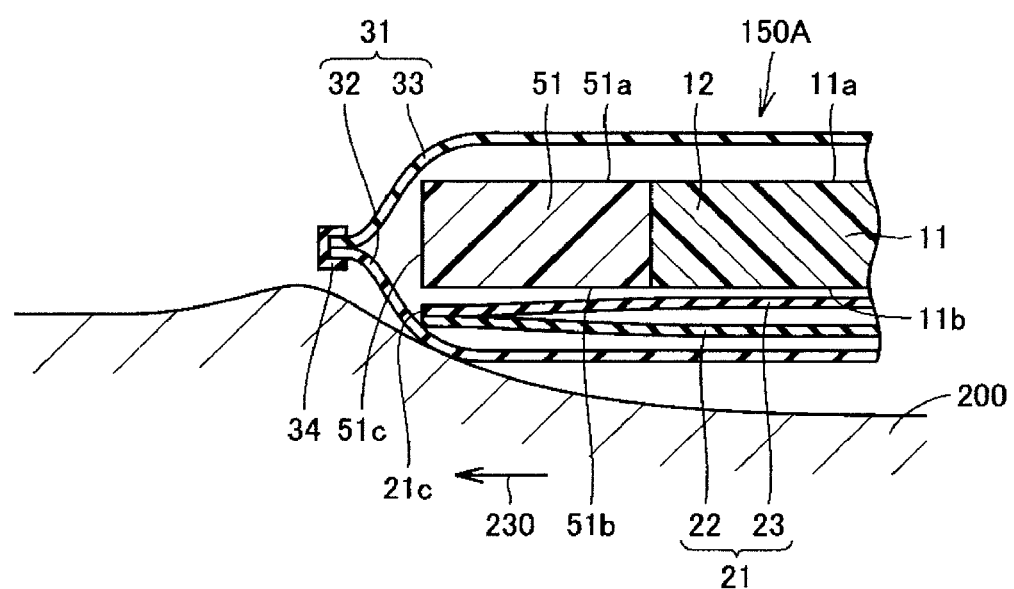
FIG. 6 is a cross-sectional view showing the sphygmomanometer cuff in a range surrounded by a chain double-dashed line VI in FIG. 5.

FIG. 6 is a cross-sectional view showing the sphygmomanometer cuff in the range surrounded by a chain double-dashed line VI in FIG. 5. In this figure, the cross-section at the end of the sphygmomanometer cuff 150A in the axis direction of the center axis 220 (hereinafter referred to as direction indicated with an arrow 230) is shown. With reference to FIG. 6, the curler 11 includes an end 12. The end 12 is arranged at the end of the curler 11 in the direction indicated with the arrow 230 with the arm 200 passing through the sphygmomanometer cuff 150A. The end 12 is arranged at the end on the side of the upper arm 210 opposite to the fingertips in the direction indicated with the arrow 230. The end 12 is arranged along the longer side of the curler 11 having a substantially rectangular outer shape with the curler 11 being in the developed state.

The sphygmomanometer cuff 150A includes a cushion material 51. The cushion material 51 is arranged at a position projecting from the end 12 in the direction indicated with the arrow 230. In other words, the cushion material 51 is arranged at a position projecting outward from the curler 11 relative to the end 12 in the direction indicated with the arrow 230. The cushion material 51 is accommodated in the bag-shaped cover body 31 with the air bladder 21 and the curler 11. The cushion material 51 is fixed to the curler 11. The cushion material 51 is arranged to overlap the air bladder 21. The cushion material 51 is arranged between the outer cover member 33 of the bag-shaped cover body 31 and the air bladder 21. In the figure, the cushion material 51 is arranged at the end 12 on the side of the upper arm 210 of the curler 11, but the cushion material 51 may also be arranged at the end on the opposite side.

The cushion material 51 has a property of being easily compression deformed relative to the curler 11. That is, when a force of the same magnitude is applied on the curler 11 and the cushion material 51 having the same outer shapes, the deformation amount of the cushion material 51 becomes greater than the deformation amount of the curler 11. The cushion material 51 is made of a foamed sponge material or an elastomer. The cushion material 51 is made of a material different from that of the curler 11. In the present embodiment, the curler 11 is made of polypropylene, whereas the cushion material 51 is made of a resin material softer than polypropylene.

According to such a configuration, the soft cushion material 51 can be brought into contact with the arm 200 when the subject passes the arm 200 through the sphygmomanometer cuff 150A in the tubular state and attaches to the upper arm 210. The end 12 of the curler 11 is thus prevented from touching the arm 200, so that the subject does not feel pain during attachment of the sphygmomanometer cuff 150A. In the present embodiment, the cushion material 51 does not be positionally shifted with respect to the curler 11 since the cushion material 51 is fixed to the curler 11. The end 12 of the curler 11 is therefore more reliably prevented from touching the arm 200.

Describing the structure of the cushion material 51 in more detail, the cushion material 51 is provided integrally with the curler 11 on the extension of the curler 11 extending in the direction indicated with the arrow 230. The curler 11 includes an outer surface 11a facing the outer cover member 33, and an inner surface 11b facing the inner cover member 32. The cushion material 51 includes an outer surface 51a facing the outer cover member 33, and an inner surface 51b facing the inner cover member 32. The cushion material 51 is arranged so that the outer surface 11a and the inner surface 11b, and the outer surface 51a and the inner surface 51b extend within a same plane. The curler 11 integrated with the cushion material 51 is manufactured by separately resin molding the curler 11, disposing the curler 11 in a die, and injecting a resin material for forming the cushion material 51 in this die. With such a configuration, the curler 11 and the cushion material 51 can be collectively handled in the assembly step of the sphygmomanometer cuff 150A. Since the cushion material 51 is arranged on the extension of the curler 11 extending in the direction indicated with the arrow 230, the curler 11 integrated with the cushion material 51 can be smoothly inserted into the bag-shaped cover body 31.

The cushion material 51 is arranged such that an end 51c of the cushion material 51 and an end 21c of the air bladder 21 in the direction indicated with the arrow 230 are aligned with each other. According to such a configuration, the size of the bag-shaped cover body 31 does not become large by the arrangement of the cushion material 51, and increase in size of the sphygmomanometer cuff 150A can be suppressed.

The sphygmomanometer cuff 150A according to the first embodiment of the present invention includes the air bladder 21 serving as a fluid bag for compressing the arm 200 and arranged around the arm 200 of the subject; the curler 11 serving as a curved elastic member elastically deformable in the radial direction thereof, arranged to overlap the outer side of the air bladder 21 with respect to the arm 200, and formed in a substantially tubular shape extending in the direction indicated with the arrow 230 along a predetermined axis direction; the cushion material 51 arranged at a position projecting from the end 12 of the curler 11 in the direction indicated with the arrow 230 and being easily compression deformable relative to the curler 11; and the bag-shaped cover body 31 accommodating the air bladder 21, the curler 11, and the cushion material 51.

According to the sphygmomanometer cuff 150A and the sphygmomanometer 100 of the first embodiment of the present invention configured as described above, the subject does not feel pain occurring when the end 12 of the curler 12 touches the arm 200 upon passing the arm 200 through the sphygmomanometer cuff 150A in the tubular state and attaching the same to the upper arm 210. The attachment feeling in time of attaching the sphygmomanometer cuff 150A thus can be enhanced.

Various variants of the sphygmomanometer cuff 150A in FIG. 5 will be described next.

Figure 7:
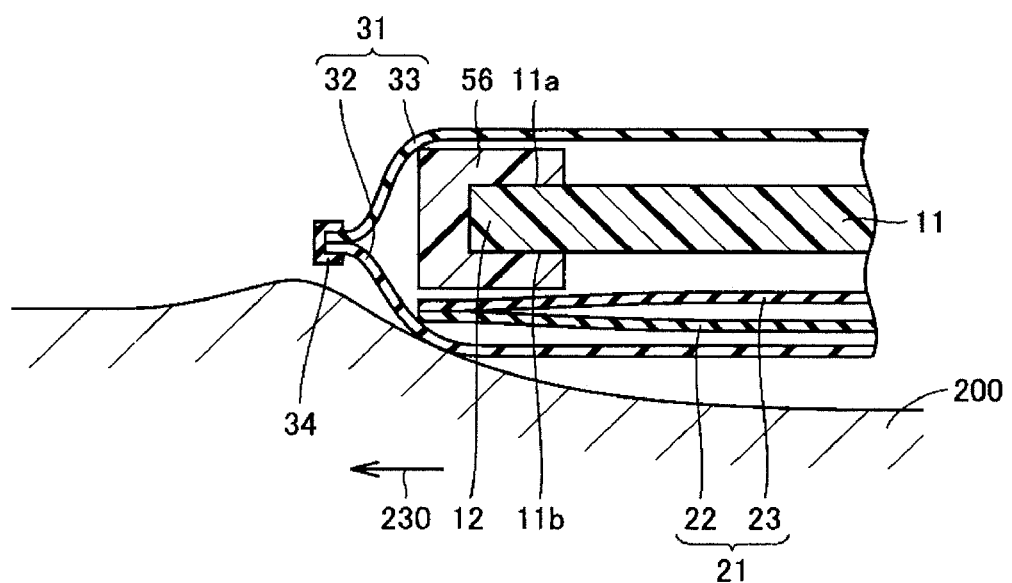
FIG. 7 is a cross-sectional view showing a first variant of the sphygmomanometer cuff in FIG. 6.
Figure 8:
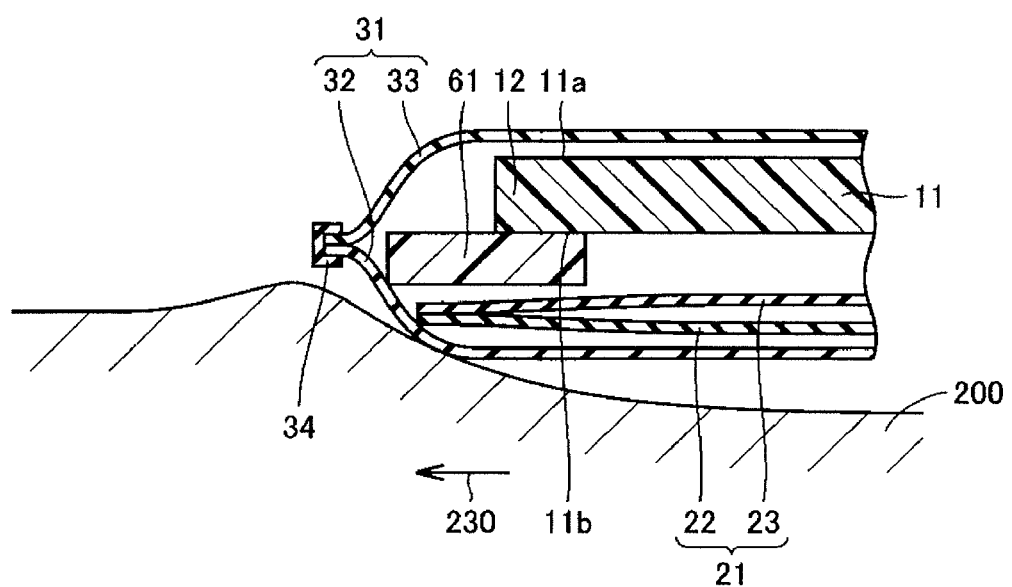
FIG. 8 is a cross-sectional view showing a second variant of the sphygmomanometer cuff in FIG. 6.

FIG. 7 is a cross-sectional view showing a first variant of the sphygmomanometer cuff in FIG. 6. With reference to FIG. 7, the sphygmomanometer cuff 150 includes a cushion material 56 in the present variant. The cushion material 56 is fixed to the curler 11 by an adhesive, for example. The cushion material 56 is arranged to cover the end 12 of the curler 11. The cushion material 56 is arranged in a range of the outer surface 11a, the end side of the end 12, and the inner surface 11b. FIG. 8 is a cross-sectional view showing a second variant of the sphygmomanometer cuff in FIG. 6. With reference to FIG. 8, the sphygmomanometer cuff 150A includes a cushion material 61 in the present variant. The cushion material 61 is arranged between the curler 11 and the air bladder 21. The cushion material 61 is joined to the inner surface 11b of the curler 11. According to the variants shown in FIG. 7 and FIG. 8, the end 12 of the curler 11 is more reliably prevented from touching the arm 200 in time of attaching the sphygmomanometer cuff 150A.

Figure 9:
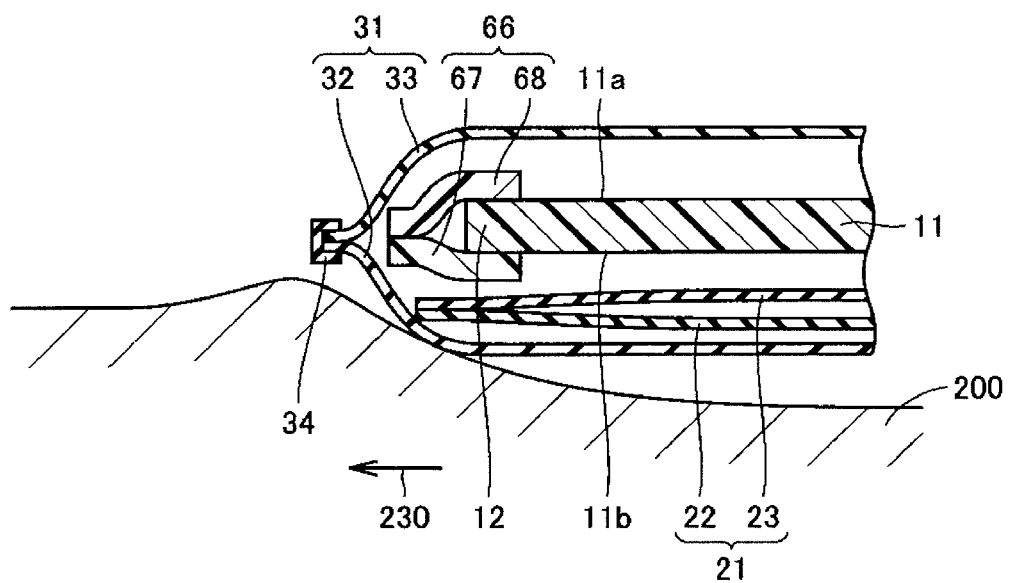
FIG. 9 is a cross-sectional view showing a third variant of the sphygmomanometer cuff in FIG. 6.

FIG. 9 is a cross-sectional view showing a third variant of the sphygmomanometer cuff in FIG. 6. With reference to FIG. 9, the sphygmomanometer cuff 150A includes a cushion material 66 in the present variant. The cushion material 66 is configured by an inner cushion material 67 serving as a first portion and an outer cushion material 68 serving as a second portion, which are arranged as members separate from each other. The inner cushion material 67 and the outer cushion material 68 may have the same shapes. The inner cushion material 67 and the outer cushion material 68 are arranged to sandwich the end 12 of the curler 11. The inner cushion material 67 is joined to the inner surface 11b of the curler 11, and the outer cushion material 68 is joined to the outer surface 11a of the curler 11. According to the present variant, the cushion material 66 that covers the end 12 of the curler 11 can have a simple configuration.

Figure 10:
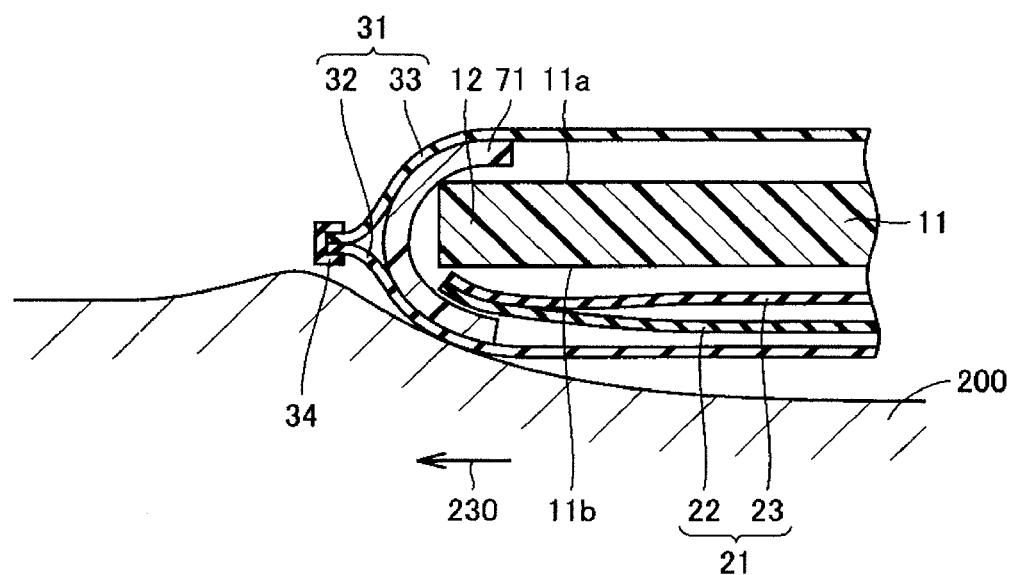
FIG. 10 is a cross-sectional view showing a fourth variant of the sphygmomanometer cuff in FIG. 6.

FIG. 10 is a cross-sectional view showing a fourth variant of the sphygmomanometer cuff in FIG. 6. With reference to FIG. 10, the sphygmomanometer cuff 150A includes a cushion material 71 in the present variant. The cushion material 71 is fixed to the bag-shaped cover body 31. The cushion material 71 is joined to the inner wall of the bag-shaped cover body 31 at a position facing the end 12.

Figure 11:
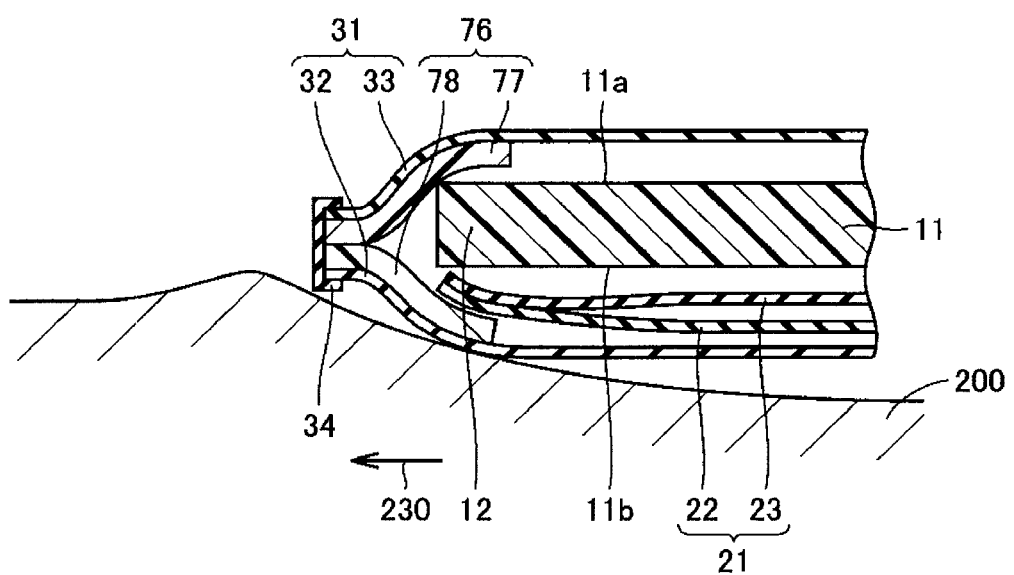
FIG. 11 is a cross-sectional view showing a fifth variant of the sphygmomanometer cuff in FIG. 6.

FIG. 11 is a cross-sectional view showing a fifth variant of the sphygmomanometer cuff in FIG. 6. With reference to FIG. 11, the sphygmomanometer 150A includes a cushion material 76 in the present variant. The cushion material 76 is configured by an inner cushion material 78 and an outer cushion material 77, which are arranged as members separate from each other. The inner cushion material 78 is fixed to the inner cover member 32, and the outer cushion material 77 is fixed to the outer cover member 33. The peripheral edges of the inner cushion material 78 and the outer cushion material 77 are overlapped with each other and joined by a bias tape 34 serving as a joining member while being sandwiched between the inner cover member 32 and the outer cover member 33.

As shown in FIG. 10 and FIG. 11, the end 12 of the curler 11 is prevented from touching the arm 200 in time of attaching the sphygmomanometer cuff 150A even with the structure in which the cushion materials 71 and 76 are fixed to the bag-shaped cover body 31. According to the variant shown in FIG. 11, the cushion material 76 can be more securely fixed to the bag-shaped cover body 31.

Figure 12:
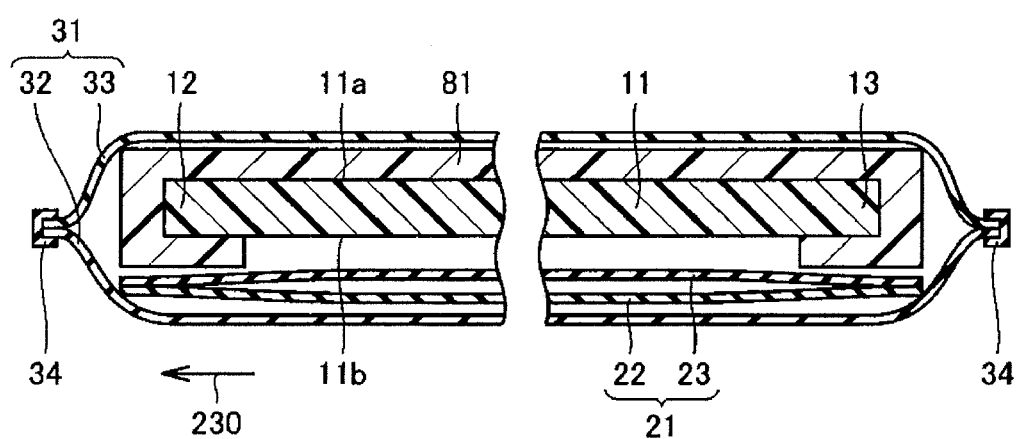
FIG. 12 is a cross-sectional view showing a sixth variant of the sphygmomanometer cuff in FIG. 6.

FIG. 12 is a cross-sectional view showing a sixth variant of the sphygmomanometer cuff in FIG. 6. With reference to FIG. 12, the curler 11 includes an end 13 arranged on the side opposite to the end 12 in the direction indicated with the arrow 230. In the present variant, the sphygmomanometer cuff 150A includes a cushion material 81 made of a foamed sponge material. The cushion material 81 is arranged at the end 12 and the end 13 in the mode same as that shown in FIG. 7. The cushion material 81 extends from the end 12 towards the end 13 so as to shield between the outer cover member 33 and the curler 11. In an alternative configuration, the end 13 may not be covered with the cushion material 81.

According to the present variant, the outer cover member 33 and the curler 11 easily slide with each other by the cushion material 81, and sudden pressure change in the cuff can be prevented in the pressurization process or the depressurization process of the sphygmomanometer cuff 150A. The blood pressure measurement of high measurement accuracy thus can be performed.

In the present embodiment, the upper arm type sphygmomanometer 150A in which the upper arm of the subject is assumed as the measuring site has been illustrated and described, but the present invention is not limited to the case and may be applied to the wrist type sphygmomanometer cuff in which a wrist is assumed as the measuring site.

Second Embodiment

Figure 13:
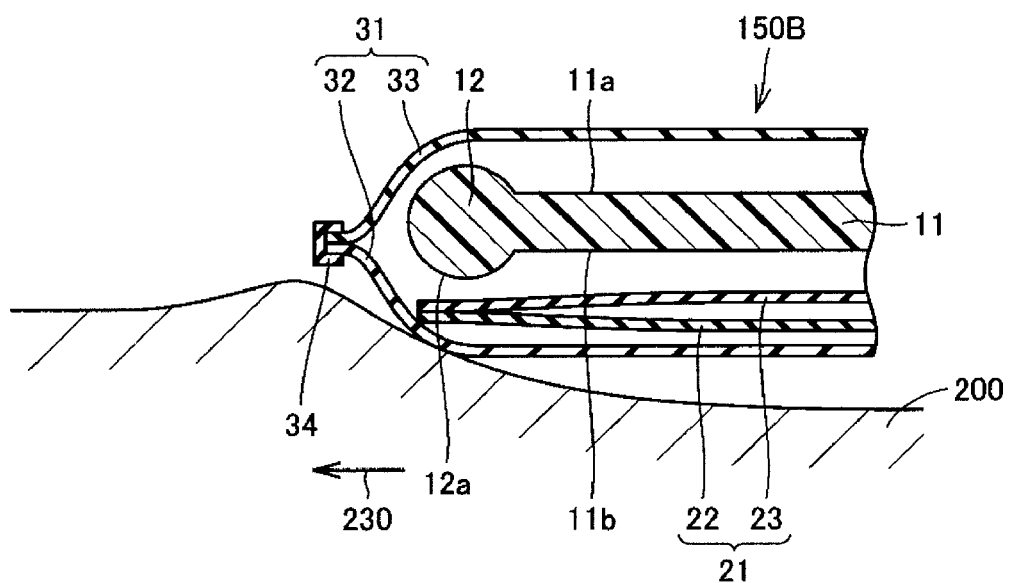
FIG. 13 is a cross-sectional view showing a sphygmomanometer cuff according to a second embodiment of the present invention.

FIG. 13 is a cross-sectional view showing a sphygmomanometer cuff according to a second embodiment of the present invention. In the figure, a cross-section at the position same as that in FIG. 6 is shown. The sphygmomanometer cuff according to the present embodiment has an overall structure similar to the sphygmomanometer cuff according to the first embodiment, and differs only in the shape of the incorporated curler. The description on the same structure will not be repeated.

With reference to FIG. 13, in the present embodiment, the end 12 of the curler 11 has a circular cross-sectional shape. The end 12 is provided with a curved surface 12a curved at a position facing the arm 200. The curved surface 12a is formed to connect the outer surface 11a and the inner surface 11b. The curved surface 12a is formed in a range greater than the space between the outer surface 11a and the inner surface 11b in the thickness direction of the curler 11.

According to such a configuration, the curved surface 12a formed on the curler 11 can be brought into contact with the arm 200 when the subject passes the arm 200 through the sphygmomanometer cuff 150B in the tubular state and attaches the same to the upper arm 210. The subject thus does not feel pain in time of attaching the sphygmomanometer cuff 150B.

The sphygmomanometer cuff 150B according to the second embodiment of the present invention includes the air bladder 21 serving as a fluid bag for compressing the arm 200 and arranged around the arm 200 of the subject; the curler 11 serving as a curved elastic member elastically deformable in the radial direction thereof, arranged to overlap the outer side of the air bladder 21 with respect to the arm 200, and formed in a substantially tubular shape extending in the direction indicated with the arrow 230 along a predetermined axis direction; and the bag-shaped cover body 31 serving as an outer package body for accommodating the air bladder 21 and the curler 11. The end 12 of the curler 11 in the direction indicated with the arrow 230 is provided with the curved surface 12a curved at a position facing the arm 200.

According to the sphygmomanometer cuff 150B of the second embodiment of the present invention configured as described above, the effects described in the first embodiment can be similarly obtained.

Various variants of the sphygmomanometer cuff 150B in FIG. 13 will be described below.

Figure 14:
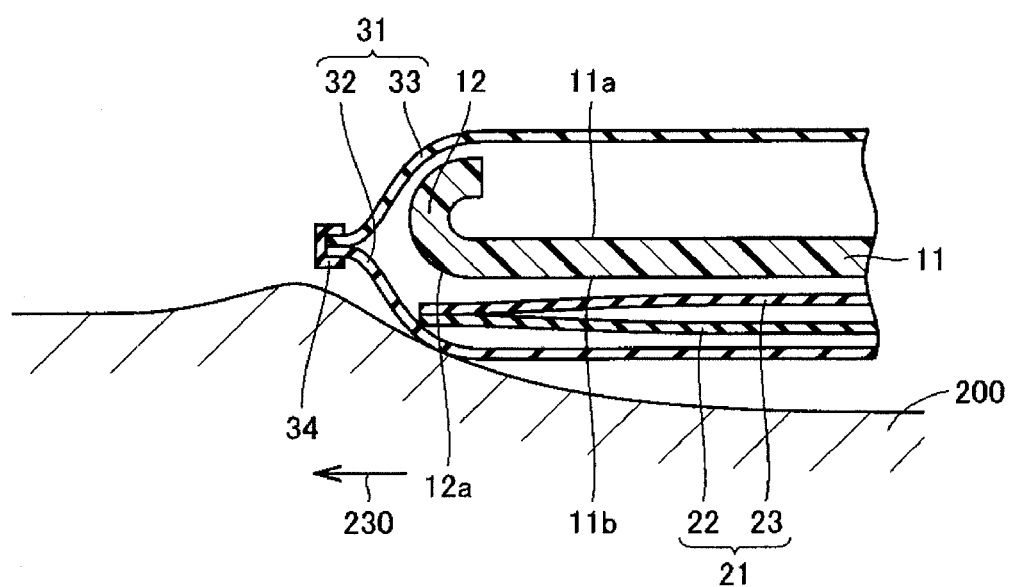
FIG. 14 is a cross-sectional view showing a first variant of the sphygmomanometer cuff in FIG. 13.

FIG. 14 is a cross-sectional view showing a first variant of the sphygmomanometer cuff in FIG. 13. With reference to FIG. 14, the end 12 of the curler 11 has a shape curved in a U-shape in the direction of moving away from the contacting surface to the arm 200 in the present variant. The end 12 is provided with the curved surface 12a curved at a position facing the arm 200. The curved surface 12a is formed in a range greater than the space between the outer surface 11a and the inner surface 11b in the thickness direction of the curler 11.

Figure 15:
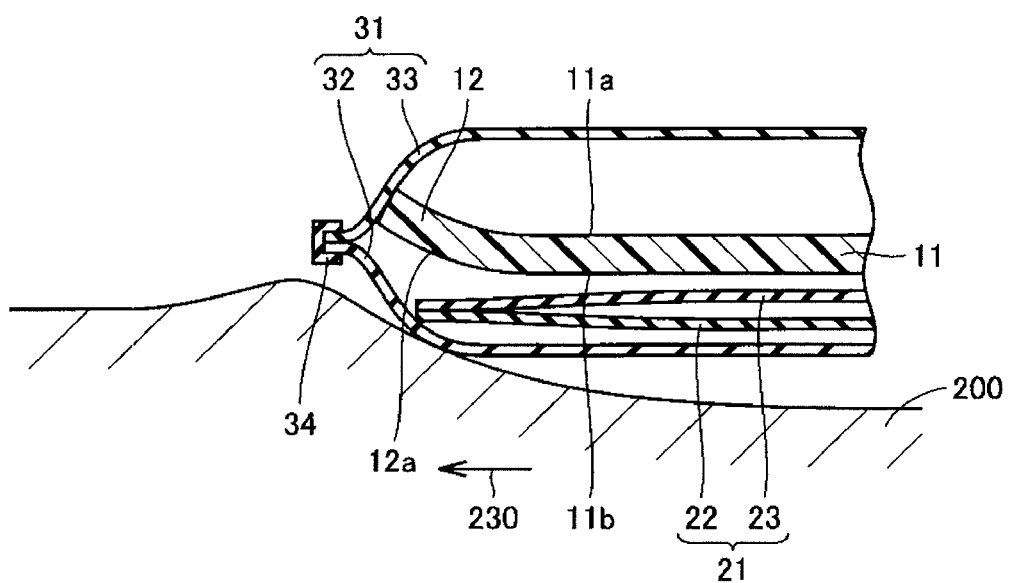
FIG. 15 is a cross-sectional view showing a second variant of the sphygmomanometer cuff in FIG. 13.

FIG. 15 is a cross-sectional view showing a second variant of the sphygmomanometer cuff in FIG. 13. With reference to FIG. 14, the end 12 of the curler 11 extends in the direction indicated with the arrow 230 while warping in the direction of moving away from the contacting surface to the arm 200 in the present variant. An end 96 is provided with a curved surface 12a curved at a position facing the arm 200. The curved surface 12a is formed in a range greater than the space between the outer surface 11a and the inner surface 11b in the thickness direction of the curler 11.

In the variants shown in FIG. 14 and FIG. 15 as well, the above-described effects can be similarly obtained by bringing the curved surface 12a into contact with the arm 200 in time of attaching the sphygmomanometer cuff 150B.

The respective configurations of the sphygmomanometer cuffs described in the above embodiments and variants may be appropriately combined to configure a new sphygmomanometer cuff.

The embodiments disclosed herein are illustrative in all aspects and should not be construed as being restrictive. The scope of the invention is defined by the Claims rather than by the description made above, and meanings equivalent to the Claims and all modifications within the scope are intended to be encompassed therein.

INDUSTRIAL APPLICABILITY

The present invention is mainly applied to an upper arm type sphygmomanometer in which the cuff is attached to the upper arm or the wrist of the subject.

The invention claimed is:

1. A sphygmomanometer cuff comprising:
a fluid bag, configured to be arranged around an arm of a subject, for compressing the arm;
an elongated curved elastic member, having opposite elongated sides connected by opposite ends, arranged to overlap an outer side of the fluid bag with respect to the arm, formed in a tubular shape extending in a predetermined axial direction, and elastically deformable in a radial direction thereof;
a cushion material arranged at a position projecting outwardly from the opposite ends of the curved elastic member in the axial direction, the cushion material being made from a material which is more easily compression deformed than a material of the curved elastic member,
wherein the cushion material is fixed to the curved elastic member; and
an outer package body for accommodating the fluid bag, the curved elastic member, and the cushion material.

2. The sphygmomanometer cuff according to claim 1, wherein the cushion material is arranged so that an end of the cushion material and an end of the fluid bag are aligned with each other in the axial direction.

3. The sphygmomanometer cuff according to claim 1, wherein the cushion material is made of a foamed sponge material or an elastomer.

4. The sphygmomanometer cuff according to claim 1, wherein the cushion material is arranged to cover the end of the curved elastic member.

5. The sphygmomanometer cuff according to claim 1, wherein the cushion material is arranged between the curved elastic member and the fluid bag.

6. The sphygmomanometer cuff according to claim 1, wherein the cushion material is provided integrally with the curved elastic member on an extension of the curved elastic member extending in the axial direction.

7. The sphygmomanometer cuff according to claim 1, wherein
the cushion material includes a first portion and a second portion arranged as members separate from each other, and
the end of the curved elastic member is sandwiched between the first portion and the second portion.

8. A sphygmomanometer using a sphygmomanometer cuff according to claim 1.

9. A sphygmomanometer cuff comprising:
a fluid bag, configured to be arranged around an arm of a subject, for compressing the arm;
an elongated curved elastic member, comprising opposite elongated sides, arranged to overlap an outer side of the fluid bag with respect to the arm, formed in a tubular shape extending in a predetermined axial direction, and elastically deformable in a radial direction thereof; and
an outer package body for accommodating the fluid bag and the curved elastic member, wherein an end of the curved elastic member in the axial direction is provided with a curved surface curved at a position facing the arm, such that a length of the curved surface is greater than a space between an outer surface and an inner surface in a thickness direction of the curved elastic member, wherein
the end of the curved elastic member has a circular cross-sectional shape.

10. The sphygmomanometer cuff according to claim 9, wherein the end of the curved elastic member extends in the axial direction while warping in a direction of moving away from a contacting surface to the arm.

11. A sphygmomanometer using the sphygmomanometer cuff according to claim 9.

12. The sphygmomanometer cuff according to claim 1, wherein the cushion material comprises a first portion and a second portion arranged as members separate from each other.

13. The sphygmomanometer cuff according to claim 1, wherein the cushion material is arranged to surround the curved elastic member at the opposite sides of the curved elastic member.

14. The sphygmomanometer cuff according to claim 1, wherein the cushion material extends between opposite sides of the curved elastic member in the axial direction so as to shield between the curved elastic member and the outer package body.

* * * * *